(12) United States Patent
Yun et al.

(10) Patent No.: US 10,064,590 B2
(45) Date of Patent: Sep. 4, 2018

(54) COMPUTED TOMOGRAPHY SYSTEM HAVING COOLING SYSTEM

(71) Applicant: SAMSUNG ELECTRONICS CO., LTD., Suwon-si (KR)

(72) Inventors: Alexander Yun, Seoul (KR); Sung-ki Kim, Seoul (KR); Il Seong, Yongin-si (KR)

(73) Assignee: SAMSUNG ELECTRONICS CO., LTD., Suwon-si (KR)

( * ) Notice: Subject to any disclaimer, the term of this patent is extended or adjusted under 35 U.S.C. 154(b) by 123 days.

(21) Appl. No.: 15/175,223

(22) Filed: Jun. 7, 2016

(65) Prior Publication Data

US 2017/0042493 A1 Feb. 16, 2017

(30) Foreign Application Priority Data

Aug. 11, 2015 (KR) .................. 10-2015-0113372

(51) Int. Cl.
*H05G 1/02* (2006.01)
*A61B 6/03* (2006.01)
*A61B 6/00* (2006.01)

(52) U.S. Cl.
CPC ........... *A61B 6/4488* (2013.01); *H05G 1/025* (2013.01); *A61B 6/035* (2013.01);
(Continued)

(58) Field of Classification Search
CPC .. A61B 6/00; A61B 6/035; A61B 6/44; A61B 6/4488; A61B 2560/00; A61B 2560/02; A61B 2560/04; A61B 2560/0406; H05G 1/00; H05G 1/02; H05G 1/025; H05G 1/04; G01N 23/00; G01N 23/046; G01N 23/08; G01N 2223/00; G01N 2223/30; G01N 2223/308; H01J 2235/00; H01J 2235/12; H01J 2235/1208;
(Continued)

(56) References Cited

U.S. PATENT DOCUMENTS 4,651,338 A 3/1987 Hahn
4,866,743 A 9/1989 Kroener
(Continued)

FOREIGN PATENT DOCUMENTS

EP 2 214 559 8/2010
JP 2001-137224 A 5/2001
(Continued)

OTHER PUBLICATIONS

Communication dated Jan. 2, 2017 issued by the European Patent Office in counterpart European Patent Application No. 16173272.2.
(Continued)

*Primary Examiner* — Anastasia Midkiff
(74) *Attorney, Agent, or Firm* — Sughrue Mion, PLLC

(57) ABSTRACT

A computed tomography (CT) system having a cooling system includes: a gantry unit, including a rotor and an assembly component; an intake provided on a first surface of the rotor; and an outtake provided on a second surface opposite to the first surface of the rotor; wherein the gantry unit is cooled by air moving through the intake and the outtake due to a rotation force or a centrifugal force generated by a rotation movement of the rotor.

19 Claims, 11 Drawing Sheets

(52) U.S. Cl.
CPC ... *A61B 2560/0406* (2013.01); *H01J 2235/12* (2013.01); *H01J 2235/127* (2013.01); *H01J 2235/1208* (2013.01); *H01J 2235/1216* (2013.01); *H01J 2235/1225* (2013.01); *H01J 2237/002* (2013.01)

(58) Field of Classification Search
CPC ....... H01J 2235/1216; H01J 2235/1225; H01J 2235/1262; H01J 2235/127; H01J 2235/16; H01J 2235/161; H01J 2235/162; H01J 2237/00; H01J 2237/002; H01J 2237/02

See application file for complete search history.

(56) References Cited

U.S. PATENT DOCUMENTS

| | | |
|---|---|---|
| 4,969,167 A | 11/1990 | Zupancic et al. |
| 5,761,269 A | 6/1998 | Sugihara et al. |
| 6,289,073 B1 | 9/2001 | Sasaki et al. |
| 6,491,428 B1 | 12/2002 | Takanashi |
| 6,909,775 B2 | 6/2005 | Ray et al. |
| 6,988,827 B2 | 1/2006 | Mueller |
| 7,410,295 B2 | 8/2008 | Distler et al. |
| 8,197,136 B2 | 6/2012 | Buettner et al. |
| 8,770,839 B2 | 7/2014 | Gregerson et al. |
| 8,895,933 B2 | 11/2014 | Guo et al. |
| 2007/0053500 A1 | 3/2007 | Distler et al. |
| 2009/0232281 A1* | 9/2009 | Jimbo ............... A61B 6/035 378/199 |
| 2011/0228910 A1* | 9/2011 | Gregerson ......... A61B 6/4488 378/200 |
| 2015/0265232 A1* | 9/2015 | Kodaira ............. A61B 6/032 378/15 |

FOREIGN PATENT DOCUMENTS

| | | |
|---|---|---|
| JP | 2001161675 A | 6/2001 |
| JP | 2011-29143 A | 2/2011 |

OTHER PUBLICATIONS

Communication dated Feb. 6, 2017 issued by the Korean Intellectual Property Office in counterpart Korean Patent Application No. 10-2015-0113372.

Communication dated Aug. 3, 2016, issued by the Korean Intellectual Property Office in counterpart Korean Application No. 10-2015-0113372.

* cited by examiner

COMPUTED TOMOGRAPHY SYSTEM HAVING COOLING SYSTEM

CROSS-REFERENCE TO RELATED APPLICATION

This application claims priority from Korean Patent Application No. 10-2015-0113372, filed on Aug. 11, 2015, in the Korean Intellectual Property Office, the disclosure of which is incorporated herein by reference in its entirety.

BACKGROUND

1. Field

Apparatuses and methods consistent with exemplary embodiments relate to computed tomography (CT) systems, and more particularly, to CT systems having a cooling system and methods of cooling the same.

2. Description of the Related Art

With advances in medical technology, various methods have been developed to obtain information about an internal body of a subject, and in particular, a tomography system is widely used to obtain such information. A representative tomography system is a computed tomography (CT) system.

A CT system is an apparatus that irradiates X-rays onto a subject at various angles, measures the X-rays that have transmitted through the subject, and displays an image by reconstructing absorption levels of the X-rays with respect to cross-sections of the subject. In an X-ray image of the related art, a 3-dimensional (3D) shape of a subject is displayed as a 2-dimensional (2D) image. However, the CT system may display a 3D shape of selected cross-sections of the subject. Accordingly, the CT system may be used to perform a more accurate diagnosis than is possible with the X-ray image of the related art. The CT system may safely and non-destructively inspect a subject, and thus, the CT system is widely used to determine an internal shape or density of an article or a subject in various industrial fields as well as in medical fields.

A gantry unit of a CT system may include various parts and the various parts including an x-ray generator mounted in the gantry unit may include a cooling system. For example, each part mounted in the gantry unit of the CT system may include at least one fan in a box. However, the individual fans of the respective parts and an exhaust fan of the gantry unit of the CT system may cause noise and vibration in the overall CT system, and thus, may reduce durability of the entire CT system.

SUMMARY

One or more exemplary embodiments may provide computed tomography (CT) systems that include an intake formed on a first surface of a rotor and an outlet formed on a second surface of the rotor of a gantry.

One or more exemplary embodiments also provide computed tomography (CT) systems that include an intake formed on a first surface of an assembly element and an outlet formed on a second surface of the assembly element of a rotor of the gantry.

One or more exemplary embodiments may provide methods of cooling a CT system having a cooling system.

Additional aspects will be set forth in part in the description which follows and, in part, will be apparent from the description, or may be learned by practice of the presented exemplary embodiments.

According to an aspect of an exemplary embodiment, a computed tomography (CT) system may include: a gantry unit that includes a rotor and at least one assembly element; at least one intake in a first surface of the rotor; and at least one outlet in a second surface of the rotor, wherein air in the gantry unit is cooled by moving through the at least one intake and the at least one outlet due to a rotation force or a centrifugal force generated by a rotation movement of the gantry unit.

The formation direction of the at least one intake may be at an angle between 0 and 90 degrees from a tangent of a rotational direction of the rotor.

The at least one intake may protrude to the outside of the first surface of the rotor.

The at least one intake may include at least one hole passing through an inside of the rotor from the first surface of the rotor, and may include a protrusion unit protruding on the first surface from a side of the at least one hole.

An upper edge of the protrusion unit may include a bending unit that is bent towards the at least one hole.

The formation direction of the at least one outlet may be at an angle between 90 and 180 degrees from a tangent of a rotational direction of the rotor.

The at least one outlet may protrude towards the inside of the rotor from the second surface of the rotor.

The at least one outlet may include at least one hole passing through the first surface of the rotor from the inside of the rotor, and may include a protrusion unit protruding towards the inside of the rotor from a side of the at least one hole.

An upper edge of the protrusion unit may include a bending unit that is bent towards the at least one hole.

The second surface may face the first surface.

The CT system may further include at least one intake in a first surface of the at least one assembly element and at least one outlet in a second surface of the at least one assembly element.

According to an aspect of another exemplary embodiment, a CT system includes: a gantry unit that may include a rotor and at least one assembly element; at least one intake in a first surface of the at least one assembly element; and at least one outlet in a second surface of the at least one assembly element, wherein air in the gantry unit is cooled by moving through the at least one intake and the at least one outlet due to a rotation force or a centrifugal force generated by a rotation movement of the gantry unit.

According to an aspect of another exemplary embodiment, a method of cooling a CT system, the method may include: moving air outside of a rotor or at least one assembly element to inside of the rotor or the at least one assembly element through at least one intake in a first surface of the rotor or the at least one assembly element of a gantry; and moving air inside of the rotor or the at least one assembly element to outside of the rotor or the at least one assembly element through at least one outlet in a second surface of the rotor or the at least one assembly element.

According to an aspect of another exemplary embodiment, a computed tomography (CT) apparatus having a cooling system may include: a gantry unit including: a rotor; and an assembly component; an intake provided on a first surface of the rotor; and an outlet provided on a second surface opposite to the first surface of the rotor, wherein the gantry unit is cooled by air moving through the intake and the outlet due to a rotation force or a centrifugal force generated by a rotation movement of the rotor.

The assembly component may be cooled by the air moving from an exterior of the rotor through the intake into the rotor and exiting the rotor through the outlet due to the rotation force or the centrifugal force generated by the rotation movement of the rotor.

The intake may extend along a radial direction of the rotor at an angle between 0 and 90 degrees from a tangent line extending along a rotational direction of the rotor, the tangent line extending from an inner surface of the rotor provided between the first and the second surfaces.

The intake may protrude toward an exterior of the first surface of the rotor.

The intake may include a through-hole passing through the first surface of the rotor, and may include a protrusion unit protruding from the first surface from a portion of the first surface adjacent to the through-hole.

A first portion of the protrusion unit may include a bending unit that is bent towards the through-hole and a second portion of the protrusion unit opposite to the first portion is attached to the first surface.

The outlet may extend along a radial direction of the rotor at an angle between 90 and 180 degrees from a tangent line extending along a rotational direction of the rotor, the tangent line extending from an inner surface of the rotor provided between the first and the second surfaces.

The outlet may protrude towards an interior of the rotor from the second surface of the rotor.

The outlet may include a through-hole passing through the second surface of the rotor, and may include a protrusion unit protruding towards the interior of the rotor from a portion of the second surface adjacent to the through-hole.

A first portion of the protrusion unit may include a bending unit that is bent towards the hole and a second portion of the protrusion unit opposite to the first portion is attached to the first surface.

The second surface may face the first surface.

The component may be mounted inside of the rotor.

The CT apparatus may further include: a component intake provided on a first surface of the component; and a component outlet provided on a second surface of the component.

According to an aspect of another exemplary embodiment, a computed tomography (CT) apparatus having a cooling system may include: a gantry unit including: a rotor; and at least one assembly element; at least one intake provided in a first surface of the at least one assembly element; and at least one outlet provided in a second surface opposite to the first surface of the at least one assembly element, wherein the gantry unit is cooled by air moving through the at least one intake and the at least one outlet due to a rotation force or a centrifugal force generated by a rotation movement of the rotor.

The at least one assembly element may be cooled by the air moving from an exterior of the gantry unit through the intake into the at least one assembly element and exiting the at least one assembly element through the outlet due to the rotation force or the centrifugal force generated by the rotation movement of the rotor.

The intake may extend along a radial direction of the rotor at an angle between 0 and 90 degrees from a tangent line extending along a rotational direction of the rotor, the tangent line extending from an inner surface of the rotor provided between the first and the second surfaces.

The at least one intake may protrude towards an exterior of the first surface of the at least one assembly element.

The at least one intake may include at least one hole passing through the first surface of the at least one assembly element towards an interior of the at least one assembly element, and may include a protrusion unit protruding on the first surface from a portion of the first surface adjacent to the at least one hole.

An upper portion of the protrusion unit may include a bending unit that is bent towards the at least one hole.

The at least one outlet may extend along a radial direction of the rotor at an angle between 90 and 180 degrees from a tangent line extending along a rotational direction of the rotor, the tangent line extending from an inner surface of the rotor provided between the first and the second surfaces.

The at least one outlet may protrude towards an interior of the at least one assembly element from the second surface of the at least one assembly element.

According to an aspect of another exemplary embodiment, a method of cooling a computed tomography (CT) apparatus may include: moving air from an exterior of a rotor or at least one assembly element of a gantry of the CT apparatus to an interior of the rotor or the at least one assembly element through at least one intake provided in a first surface of the rotor or the at least one assembly element; and moving the air provided in the interior of the rotor or the at least one assembly element to the exterior of the rotor or the at least one assembly element through at least one outlet provided in a second surface of the rotor or the at least one assembly element.

According to an aspect of another exemplary embodiment, a computed tomography (CT) apparatus having a cooling system may include: a gantry unit including: a rotor; and an assembly component; an intake unit provided on a first surface of the rotor and including: an intake through-hole; and a first protrusion protruding from the first surface of the rotor; an outlet unit provided on a second surface opposite to the first surface of the rotor and including: an outlet through-hole; and a second protrusion protruding from the second surface of the rotor toward an interior of the rotor, wherein the intake unit extends along a radial direction of the rotor at an acute angle from an intake tangent line extending along a rotational direction of the rotor, and wherein the outlet unit extends along the radial direction of the rotor at an obtuse angle from an outlet tangent line extending along the rotational direction of the rotor, the intake and the outlet tangent lines extending from an inner surface of the rotor provided between the first and the second surfaces.

The assembly component may be cooled by air moving from an exterior of the rotor through the intake unit into the rotor and exiting the rotor through the outlet unit due to the rotation force or the centrifugal force generated by a rotation movement of the rotor.

BRIEF DESCRIPTION OF THE DRAWINGS

The above and/or other aspects of the disclosure will become apparent and more readily appreciated from the following description of the exemplary embodiments, taken in conjunction with the accompanying drawings in which.

DETAILED DESCRIPTION

Figure 1:
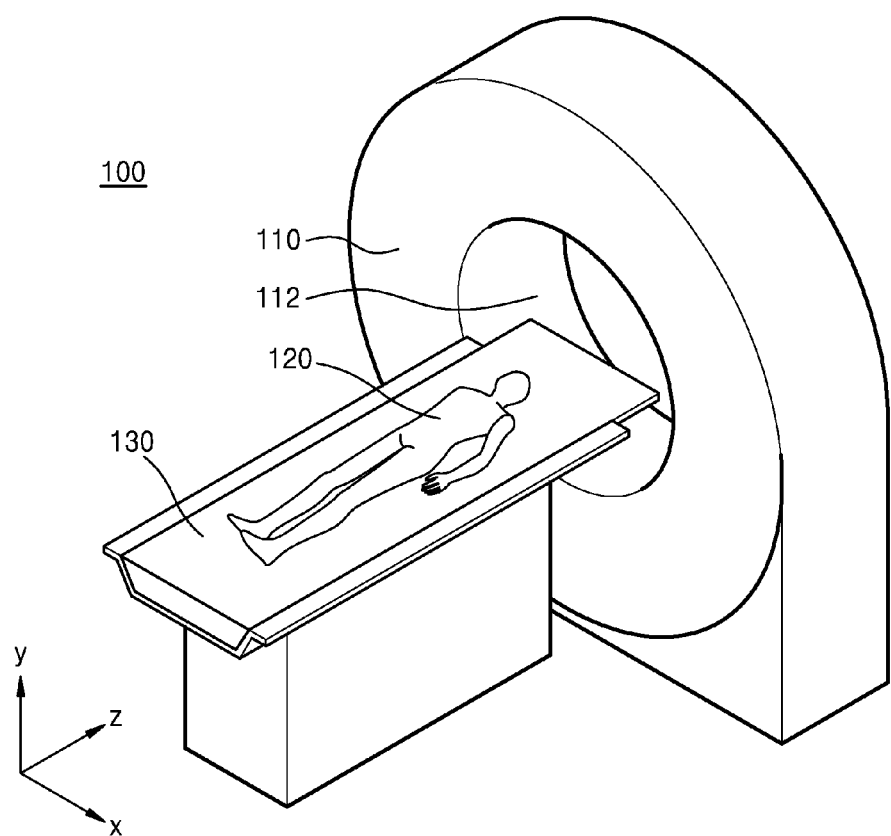
FIG. 1 is a schematic perspective view of a computed tomography (CT) system according to an exemplary embodiment.

A computed tomography (CT) system according to an exemplary embodiment will be described with reference to the accompanying drawings. In the drawings, like reference numerals refer to like elements throughout the specification and elements having like reference numerals may be formed of the same material. Also, in the drawings, thicknesses of layers and regions may be exaggerated for clarity of the layers and regions.

Figure 2:
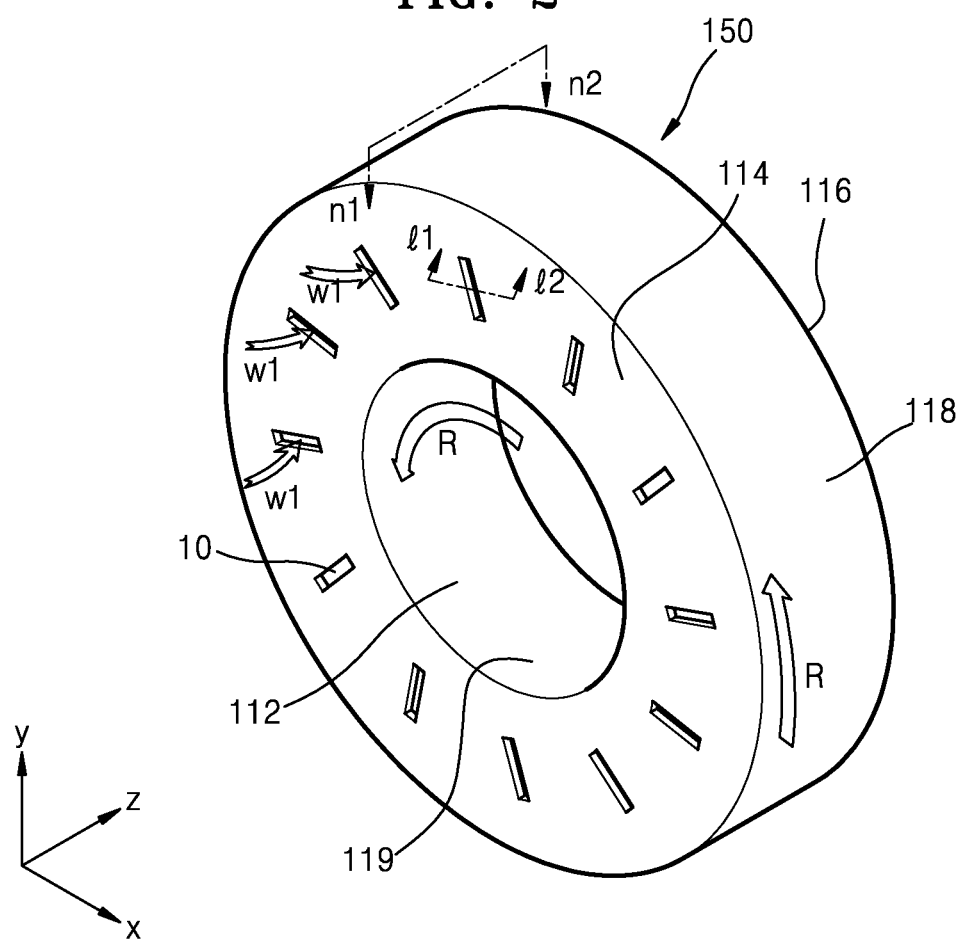
FIG. 2 is a perspective view illustrating a first surface of a rotor of a CT system according to an exemplary embodiment.
Figure 3:
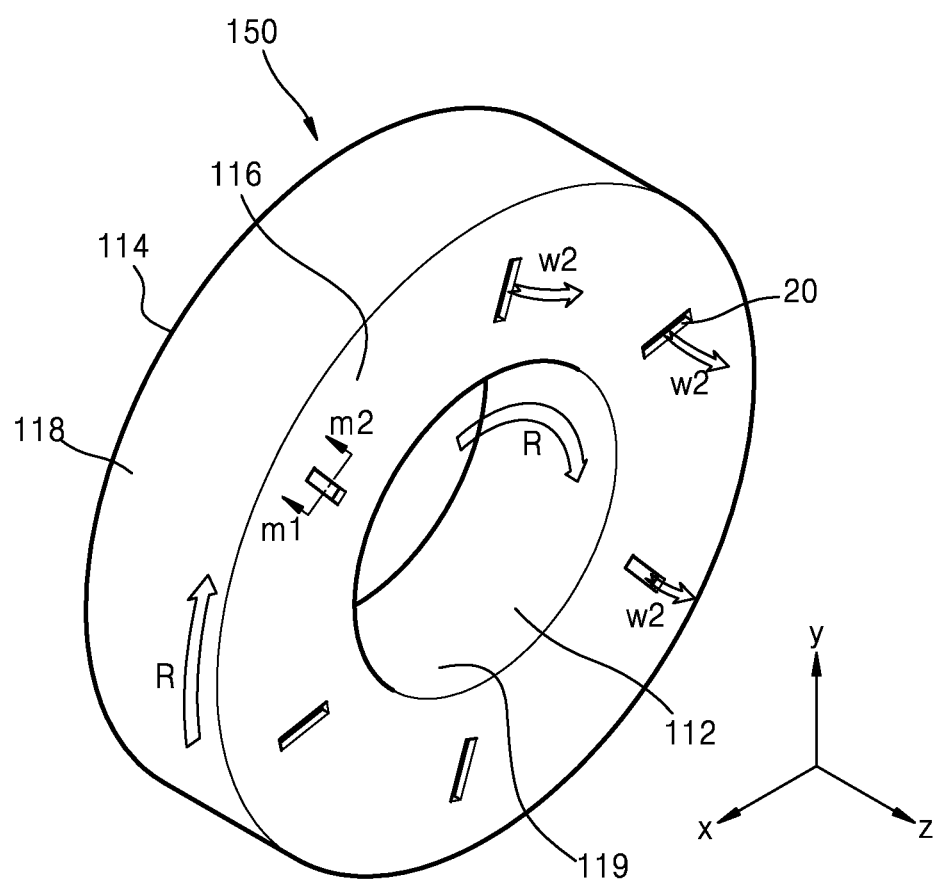
FIG. 3 is a perspective view illustrating a second surface of a rotor of a CT system according to an exemplary embodiment.

FIG. 1 is a schematic perspective view of a CT system 100 according to an exemplary embodiment. FIG. 2 is a perspective view illustrating a first surface 114 of a rotor 150 of a CT system 100 according to an exemplary embodiment. FIG. 3 is a perspective view illustrating the second surface 116 of the rotor 150 of a CT system 100 according to an exemplary embodiment.

Referring to FIG. 1, the CT system 100 according to an exemplary embodiment may include a gantry unit 110 and a table 130 that may move a subject 120 to be inspected. The gantry unit 110 may have a bore 112 having a cylindrical shape at a center thereof, and an inspection with respect to the subject 120, that is, CT imaging, may be performed by moving the table 130 on which the subject 120 is placed into the bore 112 of the gantry unit 110.

In a process of capturing a CT image with respect to the subject 120, the table 130 may be moved in at one direction of upwards, downwards, left side, or right side. The table 130 may be tilted or rotated at a predetermined angle in a predetermined direction. Also, the gantry unit 110 may be tilted or rotated at a predetermined angle in a predetermined direction.

In the exemplary embodiment, the subject 120 may be a human or an animal besides human, or a portion thereof. For example, the subject 120 may be an organ, such as, a liver, a heart, a womb, a brain, a breast, and an abdomen or blood vessels. Also, the subject 120 may include a phantom. The phantom may denote a specially designed object having a volume near to a density and an effective atom number of a living organism, and may include a sphere phantom having similar characteristics to a body.

The gantry unit 110 may include a cover unit 140 (FIG. 9) that surrounds an external surface thereof, a rotor that is formed to rotate in the cover unit, and a stator that is fixed in the cover unit not to be rotated. The rotor may include various assembly components including an X-ray generator. In detail, the assembly components included in the gantry unit 110 may be an X-ray generator, an X-ray detector, a data acquisition system (DAS), and a power supply. When the CT system 100 is in operation, various components in the gantry unit 110 are operated, and thus, the temperature in the gantry unit 110 may be increased. In the CT system 100 having a cooling system according to the exemplary embodiment, an intake 10 is formed in a first surface 114 of the rotor 150 and an outlet 20 is formed in a second surface 116 of the rotor 150, and the intake 10 and the outlet 20 may respectively intake air into the rotor of the gantry unit 110 from the outside and exhaust air in the rotor 150 of the gantry unit 110 to the outside by a rotation force or centrifugal force generated by a rotational movement of the rotor 150, which will be described in detail below.

Referring to FIGS. 1 and 2, the rotor 150 mounted in the gantry unit 110 may include the first surface 114, a second surface 116, and a third surface 118 and a fourth surface 119 provided between the first surface 114 and the second surface 116. Specifically, the third surface corresponds to an outer-most surface of the rotor 150 and the fourth surface 119 corresponds to an inner-most surface of the rotor forming a bore 112 of the rotor 150. The first surface 114 and the second surface 116 may face each other. Here, the first surface 114 is located on a surface having an entrance for the table 130 on which the subject 120 is placed to enter into the gantry unit 110. The first surface 114 may be referred to as a front surface and the second surface 116 opposing the first surface 114 may be referred to as a rear surface. However, the exemplary embodiment is not limited thereto. For example, the second surface 116 may be a surface having a surface having an entrance for the subject 120 to enter into the bore 112 of the gantry unit 110 while the first surface 114 may be a surface corresponding to a surface opposite to the second surface 116 through which the subject 120 enters into the bore 112 of the gantry unit 110. In the exemplary embodiment, at least one intake 10 may be formed in the first surface 114 of the rotor 150. The intake 10 may correspond to a through-hole passing through the first surface 114 of the rotor 150 between an exterior of the rotor 150 and an interior of the rotor 150. When the CT system 100 is operated as the subject 120 placed on the table 130 enters into the bore 112 of the gantry unit 110, the rotor 150 may have a rotational movement in a direction indicated by R and air outside the rotor 150 may move in a direction W1 to the inside of the rotor 150 through the intake 10. The size (length and width) of the intake 10 formed on the first surface 114 of the rotor 150 is not particularly limited, and also, the number of intakes 10 is not particularly limited.

Referring to FIGS. 1 and 3, at least one outlet 20 may be formed in the second surface 116 of the rotor 150. The outlet 20 may correspond to a through-hole passing through the second surface 116 of the rotor 150 between an exterior of the rotor 150 and an interior of the rotor 150. When the CT system 100 is operated, the rotor 150 may have a rotational movement in a direction indicated by R and air inside the rotor 150 may move in a direction W2 to the exterior of the rotor 150 through the outlet 20. The size (length or width) of the outlet 20 formed in the second surface 116 of the rotor 150 is not particularly limited, and the number of outlets 20 formed in the second surface 116 of the rotor 150 is not particularly limited.

Referring to FIGS. 1 through 3, when the CT system 100 is operated, the rotor 150 inside the gantry unit 110 may have a rotational movement in a direction indicated by R, and air outside the rotor 150 may move to the inside of the rotor 150 through the intake 10 formed on the first surface 114 of the rotor 150. Air inside the rotor 150 may move to the exterior of the rotor 150 through the outlet 20. The rotor 150 may include a plurality of assembly components inside the rotor 150, such as an X-ray generator, an X-ray detector, and a DAS, and when the CT system 100 is operated, an internal temperature of the rotor 150 may be increased due to heat emission from the various components of the rotor 150. In order to reduce the temperature inside of the rotor 150, a plurality of exhaust fans may be mounted inside the rotor 150 to exhaust the air inside the rotor 150 to the outside of the rotor 150. When the exhaust fans are operated, there is a high possibility of noise and vibration generation during the operation of the CT system 100. In the CT system 100 according to the exemplary embodiment, at least one intake 10 is formed on the first surface 114 and at least one outlet 20 is formed on the second surface 116 of the rotor 150, and thus, the temperature inside the rotor 150 may be reduced by intaking cool air from the exterior of the rotor 150 to cool the various components and exhausting heated internal air that has a relatively higher temperature than the external air to the outside of the rotor 150.

Figure 4A:
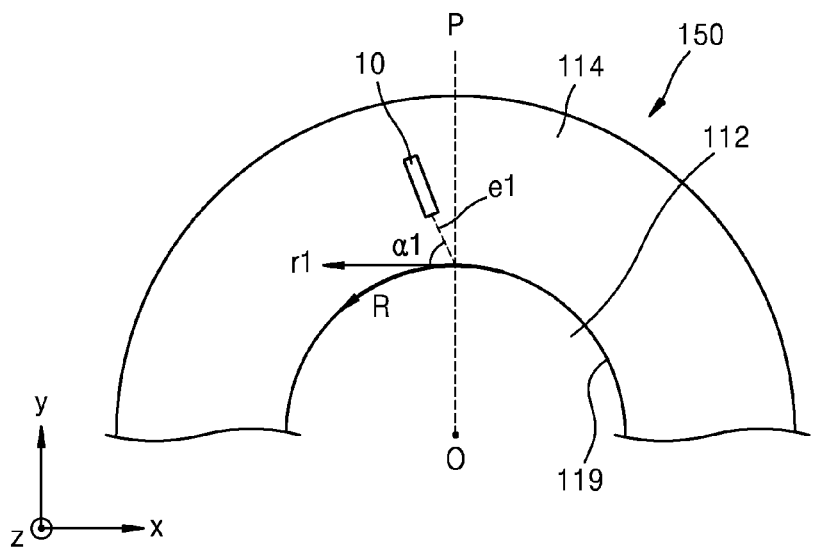
FIG. 4A is a drawing for explaining a formation principle of an inhale port formed in a first surface of the rotor of the CT system of FIG. 2.

FIG. 4A is a drawing for explaining a formation principle of the intake 10 formed through the first surface 114 of the rotor 150 of the CT system 100 of FIG. 2.

Referring to FIG. 4A, the intake 10 formed through the first surface 114 of the rotor 150 may be formed to be extending at an angle between 0 and 90 degrees)($0°<\alpha1<90°$ from a direction of a tangent line r1 extending along the rotational direction R of the rotor 150 in a radial cross-sectional view of the rotor 150 as shown in the figure. Here, the tangent line r1 starts from a point where a radial line e1 from the intake 10 extending along a radial extension direction of the intake 10 intersects the third surface 119 (i.e., the inner-most surface) of the rotor 150. The tangent line r1 may perpendicularly cross a straight line P extending from the center O of the rotational movement of the rotor 150 towards the rotor 150 at the intersection between the tangent line r1 and the radial line e1. The intake 10 is formed to have an angle between 0 and 90 degrees (i.e., having an acute angle) from the tangent line r1 starting from a point where the radial line e1 from the intake 10 extending along a radial extension direction of the intake 10 intersects the third surface 119 of the rotor 150, and thus, air outside the rotor 150 may be moved to the inside of the rotor 150 due to a rotational force or a centrifugal force generated by a rotational movement of the rotor 150.

Figure 4B:
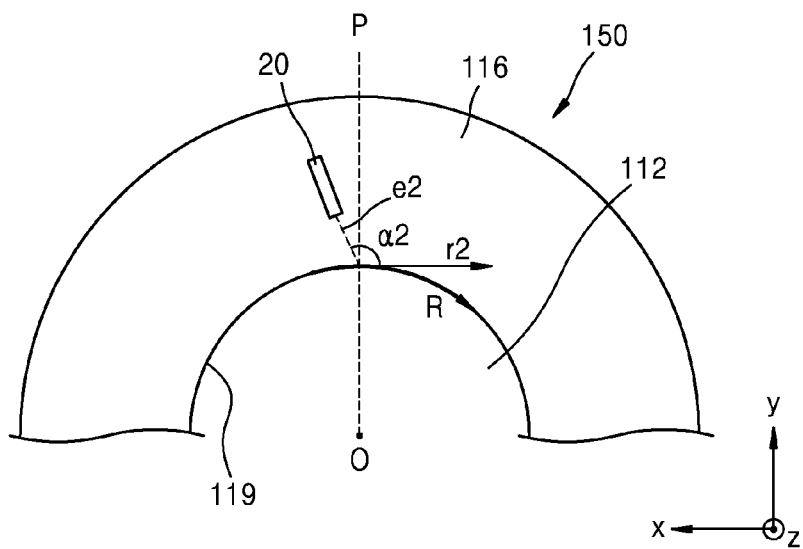
FIG. 4B is a drawing for explaining a formation principle of an exhaust port formed in a second surface of the rotor of the CT system of FIG. 3.

FIG. 4B is a drawing for explaining a formation principle of the outlet 20 formed in the second surface 116 of the rotor 150 of the CT system 100 of FIG. 3.

Referring to FIG. 4B, the outlet 20 formed through the second surface 116 of the rotor 150 may be formed to be extending at an angle between 90 and 180 degrees) ($90°<\alpha2<180°$ from a direction of a tangent line r2 extending along the rotational direction R of the rotor 150 in a radial cross-sectional view of the rotor 150 as shown in the figure. Here, the tangent line r2 starts from a point where a radial line e2 from the outlet 20 extending along a radial extension direction of the outlet 20 intersects the third surface 119 (i.e., the inner-most surface) of the rotor 150. The tangent line r1 may perpendicularly cross a straight line P extending from the center O of the rotational movement of the rotor 150 towards the rotor 150 at the intersection between the tangent line r1 and the radial line e1. The outlet 20 is formed to have an angle between 90 and 180 degrees (i.e., having an obtuse angle) from the tangent line r2 starting from a point where the radial line e2 from the outlet 20 extending along a radial extension direction of the outlet 20 intersects the third surface 119 of the rotor 150, and thus, air inside the rotor 150 may be moved to the outside of the rotor 150 due to a rotational force or a centrifugal force generated by a rotational movement of the rotor 150.

Figure 5:
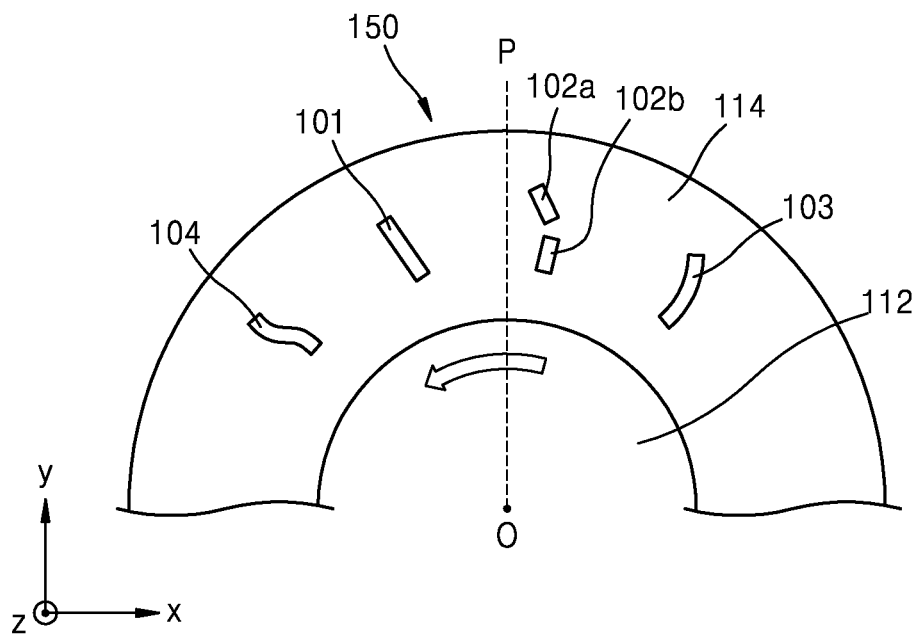
FIG. 5 is a drawing illustrating various shapes of inhale ports formed in a first surface of a rotor of a CT system according to an exemplary embodiment.

FIG. 5 is a drawing illustrating various shapes of intakes 10 formed in the first surface 114 of the rotor 150 of a CT system 100 according to an exemplary embodiment.

Referring to FIGS. 2 and 5, the intake 10 formed in the first surface 114 of the rotor 150 may be formed in various shapes without any additional limitation except for the radial extension direction of the intake 10. For example, a first intake 101 may be formed having a straight line shape. Also, second intakes 102a and 102b may be formed to include a plurality of intakes formed at different angles from each other. The efficiency of moving external air to the inside of the rotor 150 may vary according to the angle of formation and the rotation speed (rotation per minute (RPM)) of the rotor 150. Accordingly, when the rotor 150 has a rotational movement at various speeds, the rotor 150 may include a plurality of intakes formed at different angles from each other like the second intakes 102a and 102b. The intake 10 may not necessarily have a straight line shape, but may have a curved line shape having various curvatures. For example, the intake 10 may be formed as a curved line shape having a single curvature like a third intake 103 or a curved line shape in which the curvature is varied like a fourth intake 104.

The shapes of the intakes 101, 102a, 102b, 103, and 104 described above may be applied to the shape of the outlet 20. That is, the outlet 20 may be formed as a straight line shape or a curved line shape, and may be formed by including a plurality of outlets 20 having angles different from each other.

Figure 6A:
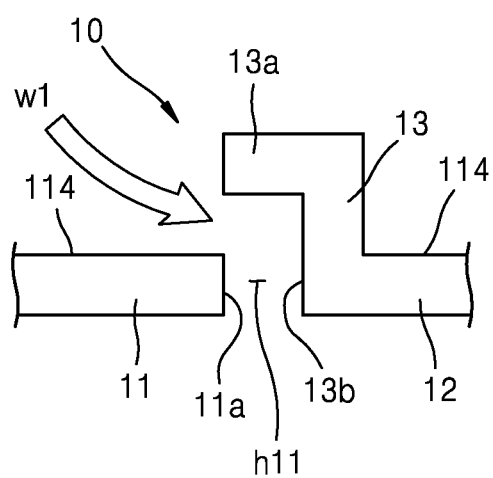
FIGS. 6A through 6D are cross-sectional views of inhale ports formed in a first surface of a rotor of a CT system according to an exemplary embodiment.

FIGS. 6A through 6D are cross-sectional views of the intake 10 formed in the first surface 114 of the rotor 150 of a CT system 100 according to an exemplary embodiment. For example, FIG. 6A is a cross-sectional view taken along a line 11-12 of the rotor 150 of FIG. 2.

Referring to FIGS. 2 and 6A, the intake 10 formed on the rotor 150 may include a through-hole h11 that passes through the first surface 114 of the rotor 150. Also, the intake 10 may include a protrusion unit 13 protruding from the first surface 114 of the rotor 150 from a first side 12 of the first surface 114 provided adjacent to the through-hole h11. An upper portion of the protrusion unit 13 may include a bending unit 13a that is bent to have a "¬" shape towards the through-hole h11, and the bending unit 13a may be formed to cover/overlap the through-hole h11. The protrusion unit 13 is formed on the first side 12 among the first and the second sides 11 and 12 and the bending unit 13a is formed on the upper portion of the protrusion unit 13, and thus, air outside the rotor 150 may be readily moved in a direction W1 to the inside of the rotor 150 by the rotational movement of the rotor 150 in the direction R.

The intake 10 may have various shapes. The protrusion unit 13 formed on the first side 12 of the through-hole h11 of FIG. 6A extends vertically (axially) and circumferentially formed from the first surface 114 of the rotor 150, and both side surfaces 11a and 13b of the through-hole h11 may be perpendicularly formed with respect to the first surface 114 of the rotor 150. However, the shape of the hole h11 is not limited thereto, but may be formed in various ways. The shapes of the intake 10 will be described with reference to FIGS. 6B through 6D.

Figure 6B:
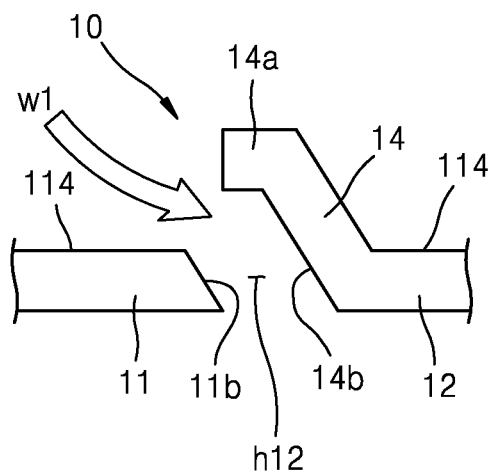

Referring to FIGS. 2 and 6B, the intake 10 may include a through-hole h12 that passes through the first surface 114 of the rotor 150. The intake 10 may also include a protrusion unit 14 protruding from the first surface 114 of the rotor 150 on a first side 12 of the though-hole h12. An upper portion of the protrusion unit 14 may include a bending unit 14*a* that extends towards the though-hole h12. Unlike the protrusion unit 13 of FIG. 6A, the protrusion unit 14 of FIG. 6B may be formed to be slanted toward a moving direction W1 of external air towards the rotor 150. Both side surfaces 14*a* and 14*b* of the hole h12 may be formed to be slanted similar to the protrusion unit 14.

Figure 6C:
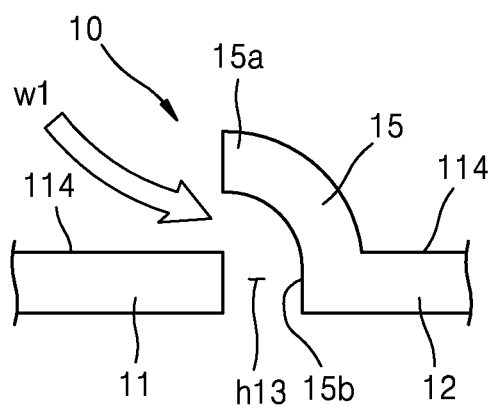

Referring to FIGS. 2 and 6C, the intake 10 may include a through-hole h13 that passes through the first surface 114 of the rotor 150. Also, the intake 10 may include a protrusion unit 15 protruding from the first surface 114 of the rotor 150 on a first side 12 of the hole h13. An upper portion of the protrusion unit 15 may include a bending unit 15*a* that is bent towards the through-hole h13. Unlike the protrusion unit 13 of FIG. 6A, the protrusion unit 15 of FIG. 6C may include a bending unit 15*a* that is bent to have a round shape. Air outside the rotor 150 may move in a direction W1 to the inside of the rotor 150 through the hole h13 along a side surface 15*b* of the protrusion unit 15.

Figure 6D:
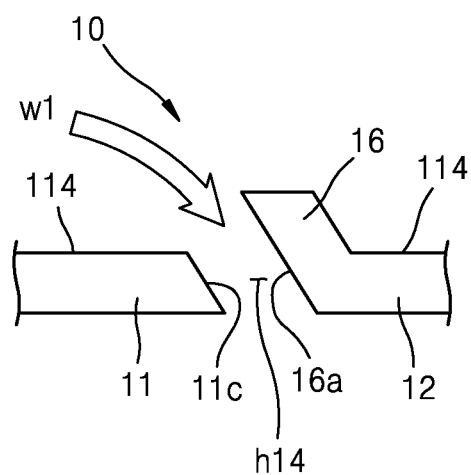

Referring to FIGS. 2 and 6D, the intake 10 may include a through-hole h14 that passes through the rotor 150 from the first surface 114 of the rotor 150. The intake 10 may also include a protrusion unit 16 protruding from the first surface 114 of the rotor 150 on a first side 12 of the through-hole h14. The protrusion unit 16 may be formed to be slanted in a direction towards the moving direction W1 of external air to the rotor 150. Both side surfaces 11*c* and 16*a* of the hole 14 may be formed to be slanted like the protrusion unit 16. The protrusion unit 16 may be formed not to include a bending unit.

FIGS. 7A through 7D are cross-sectional views of the outlets 20 formed in the second surface 116 of the rotor 150 of a CT system 100 according to an exemplary embodiment. Here, FIGS. 7A through 7D are cross-sectional views taken along a line m1-m2 of FIG. 3.

Figure 7A:
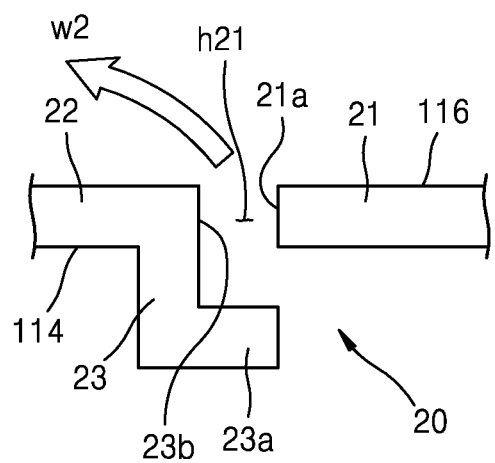
FIGS. 7A through 7D are cross-sectional views of exhaust ports formed in a second surface of a rotor of a CT system according to an exemplary embodiment.

Referring to FIGS. 3 and 7A, the outlet 20 formed on the rotor 150 may include a through-hole h21 that passes through the second surface 116 of the rotor 150. The outlet 20 may also include a protrusion unit 23 protruding towards inside of the rotor 150 from a side 22 among both sides 21 and 22 of the through-hole h21. A lower edge of the protrusion unit 23 may include a vending unit 23*a* that is bent to have a " ⌐ " shape towards the through-hole h21. Because the bending unit 23*a* is formed on the lower edge of the protrusion unit 23 protruded towards the inside of the rotor 150, air inside the rotor 150 may be readily moved along a direction W2 to the outside of the rotor 150 by the rotational movement of the rotor 150 in the direction R.

Like the intake 10, the outlet 20 may also be modified in various shapes. The protrusion unit 23 formed towards the inside of the rotor 150 is formed vertically (axially) downwards (toward the inner portion) of the rotor 150 as an example, and both side surfaces 21*a* and 23*b* of the through-hole h21 may be vertically (perpendicularly) formed with respect to the second surface 116 of the rotor 150. However, the shape of the outlet 20 is not limited thereto, and may be modified to have various shapes. The shapes of the outlets 20 will be described with reference to FIGS. 7B through 7D.

Figure 7B:
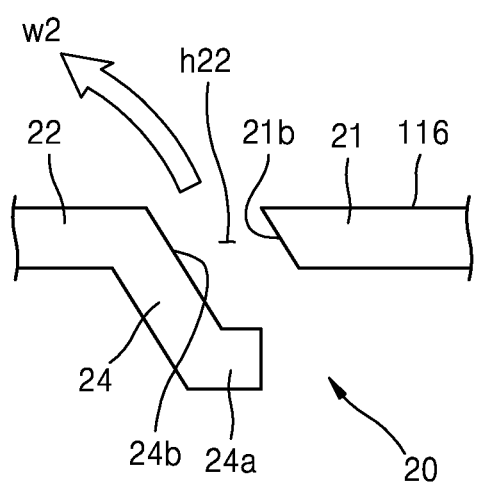

Referring to FIGS. 3 and 7B, the outlet 20 may include a through-hole h22 that passes through the second surface 116 of the rotor 150. Also, the outlet 20 may include a protrusion unit 24 protruding towards inside of the rotor 150 from a side 22 of the through-hole h22. A bending unit 24*a* that is bent in a direction towards the through-hole h22 may be formed on a lower edge of the protrusion unit 24. Unlike the protrusion unit 23 of FIG. 7A, the protrusion unit 24 of FIG. 7B may be formed to be slanted to correspond to a moving direction W1 of internal air to the outside of the rotor 150. Both side surfaces 21*b* and 24*b* of the hole h22 may also be formed to be slanted corresponding to a protruding direction of the protrusion unit 24.

Figure 7C:
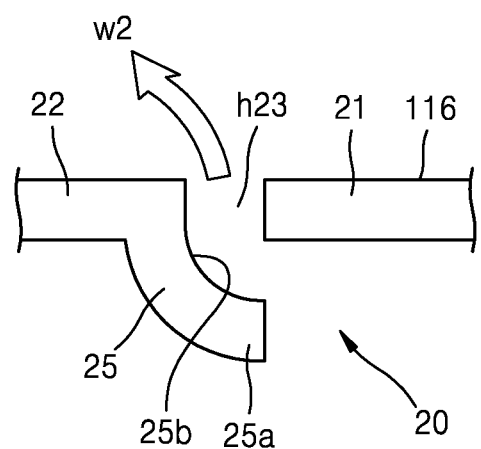

Referring to FIGS. 3 and 7C, the outlet 20 may include a through-hole h23 that passes through the second surface 116 of the rotor 150. The outlet 20 may also include a protrusion unit 25 protruding towards the inside of the rotor 150 from a side 22 of the hole h23. A bending unit 25*a* that is bent towards the through-hole h23 may be formed on a lower edge of the protrusion unit 25. Unlike the protrusion unit 23 of FIG. 7A, the protrusion unit 25 of FIG. 7C may include a bending unit 25*a* that has a round shape and is bent towards the through-hole h23. Air inside the rotor 150 may move in a direction W2 to the outside of the rotor 150 through the through-hole h23 along a side surface 25*b* of the protrusion unit 25.

Figure 7D:
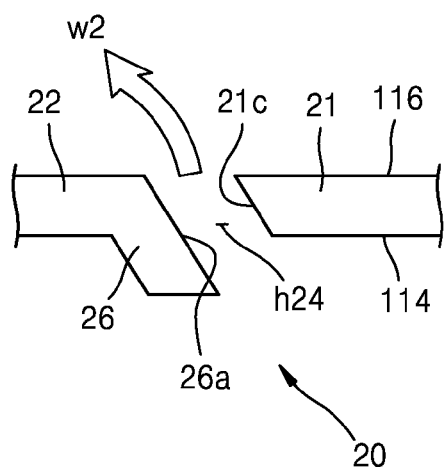

Referring to FIGS. 3 and 7D, the outlet 20 may include a hole h24 that passes through the second surface 116 of the rotor 150. The outlet 20 may also include a protrusion unit 26 protruding towards the inside of the rotor 150 from the side 22 of the hole h24. The protrusion unit 26 may be formed to be slanted towards the moving direction W2 of internal air of the rotor 150 to the outside of the rotor 150. The protrusion unit 26 of FIG. 7D may be formed not to include a bending unit.

Figure 8:
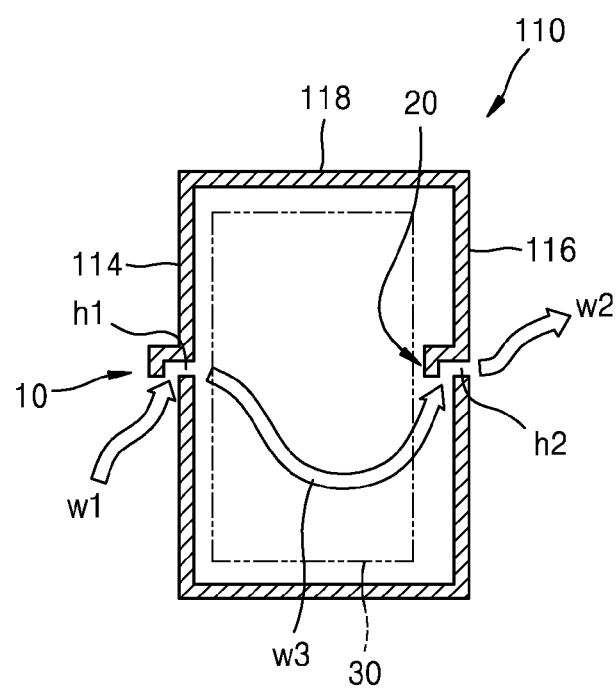
FIG. 8 is a cross-sectional view of a rotor of a CT system taken along a line n1-n2 of FIG. 2.

FIG. 8 is a cross-sectional view of a rotor of a CT system 100 taken along a line n1-n2 of FIG. 2.

Referring to FIG. 8, the intake 10 through which air outside of the rotor 150 may move in a direction W1 toward the inside of the rotor 150 may be formed in the first surface 114 of the rotor 150 of a CT system 100 according to the exemplary embodiment. When the CT system 100 is in operation, as depicted in FIG. 2, the rotor 150 may rotate in the direction indicated by R. External air may be moved in a direction W1 to the inside of the rotor 150 through a hole h1 of the intake 10 due to a rotation force or a centrifugal force generated by the rotational movement of the rotor 150. Various assembly components 30, such as, an X-ray generator, an X-ray detector, or a DAS may be provided inside the rotor 150. External air that is moved along a direction W1 to the inside of the rotor 150 from the outside of the rotor 150 through the intake 10 may cool down the assembly components 30 by moving the air inside the rotor 150 along a direction W3 inside the rotor 150, and afterwards, the air is moved along a direction W2 to the outside of the rotor 150 through the outlet 20.

When the CT system 100 is in operation, temperatures of the various assembly components 30 inside the rotor 150 may be increased, and the temperature inside of the rotor 150 may be relatively higher than an external air temperature outside the rotor 150. External air having a low temperature is moved along a direction W1 into the rotor 150 through the intake 10 of the rotor 150, and thus, the air inside of the rotor 150 may be cooled. When the inside of the rotor 150 is cooled using external air moving through the intake 10 having a protrusion unit protruding from the first surface 114 of the rotor 150 and the outlet 20 having a protrusion unit protruding inwards of the rotor 150 from the second surface 116 of the rotor 150, an additional cooling fan in the rotor 150 may no longer be necessary or the number of additional cooling fans in the rotor 150 may be reduced. In the case of a CT system of the related art, assembly components in a rotor respectively have a cooling fan, and when the CT system is in operation, inside of the CT system is cooled by operating the cooling fans. When the necessity of additional cooling fans is reduced, the number of required cooling fans may be reduced. Accordingly, sounds or noise and vibration that may occur by the operation of the fans may be removed or reduced.

In the CT system having a cooling system according to the exemplary embodiment, an air flow may be induced from the outside of the rotor 150 to the inside of the rotor 150 or from the inside of the rotor 150 to the outside of the rotor 150 by using the intake 10 formed in the first surface 114 of the housing of the rotor 150 and the outlet 20 formed in the second surface 116 of the rotor 150. The assembly components 30 mounted in the rotor 150 may have a box type frame in which various parts are stored, but, in consideration of cooling efficiency, the assembly components 30 may be mounted in the rotor 150 without including a box type housing. The housing of the rotor 150 may be formed of plastic or insulating resin.

Figure 9:
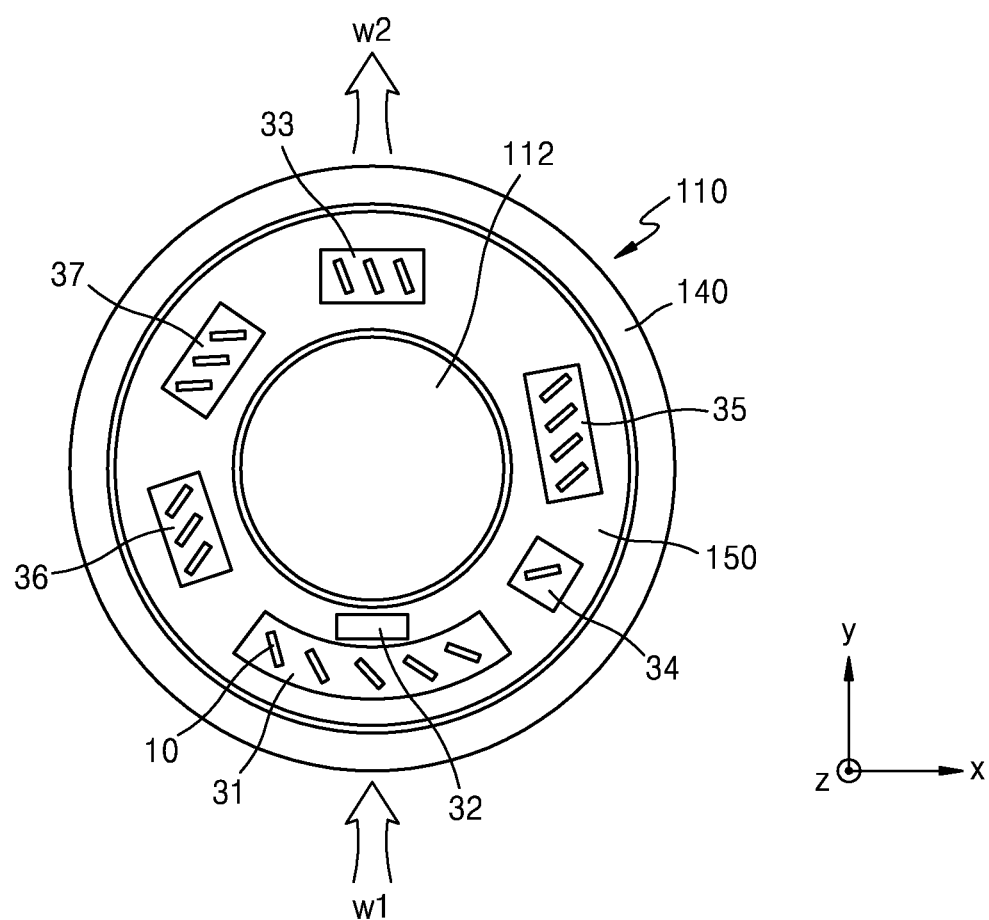
FIG. 9 is a drawing illustrating a rotor and assembly elements formed in the rotor of a gantry unit of a CT system according to an exemplary embodiment.

FIG. 9 is a drawing illustrating the rotor 150 and the assembly components 30 formed in the rotor 150 of the gantry unit 110 of a CT system according to an exemplary embodiment.

Referring to FIG. 9, the gantry unit 110 is formed in a cover unit 140 and may include the rotor 150 that rotates with respect to the bore 112. As described above, various assembly components 30 for operating the CT system may be mounted in the rotor 150. The assembly components 30 may include, for example, a DAS 31, an X-ray detector 32, an X-ray generator 33, an HVG1 34, an HVG2 35, a power supply 36, PCS 37 or HX. The assembly components may be formed without having additional box type housings in the exemplary embodiment, or may include a box type housing formed of a metal or plastic and various parts formed in the housing. If the assembly components include box type housings, intakes 10 and outlets 20 may also be formed in the box type housings. With regards to the shapes of the intake 10 and the outlet 20 formed on the assembly elements, the same shapes of the intake 10 and the outlet 20 described above may be applied.

In FIG. 9, the plural assembly components are depicted as being formed with box type housings and intakes 10 are depicted as being formed in surfaces of the box type housings, that is, in first surfaces of the assembly components. Also, outlets 20 may be formed in second surfaces facing the first surface of the assembly components. That is, a rotor and assembly components formed in the rotor of a CT system according to the exemplary embodiment may include intakes formed in first surfaces and outlets formed in second surfaces of the rotor and the assembly elements. Because an intake and an outlet are respectively formed in a first surface and a second surface of each of the assembly components in the rotor 150, when a CT system is in operation, external air may be moved into the assembly components through the intake formed in the first surface of at least one of the assembly components, and air inside of the assembly components may be moved to the outside of the assembly components through the outlets formed in the second surface of at least one of the assembly components. Accordingly, various components in a gantry unit may be cooled, and the performance of the assembly components may be maintained.

Figure 10:
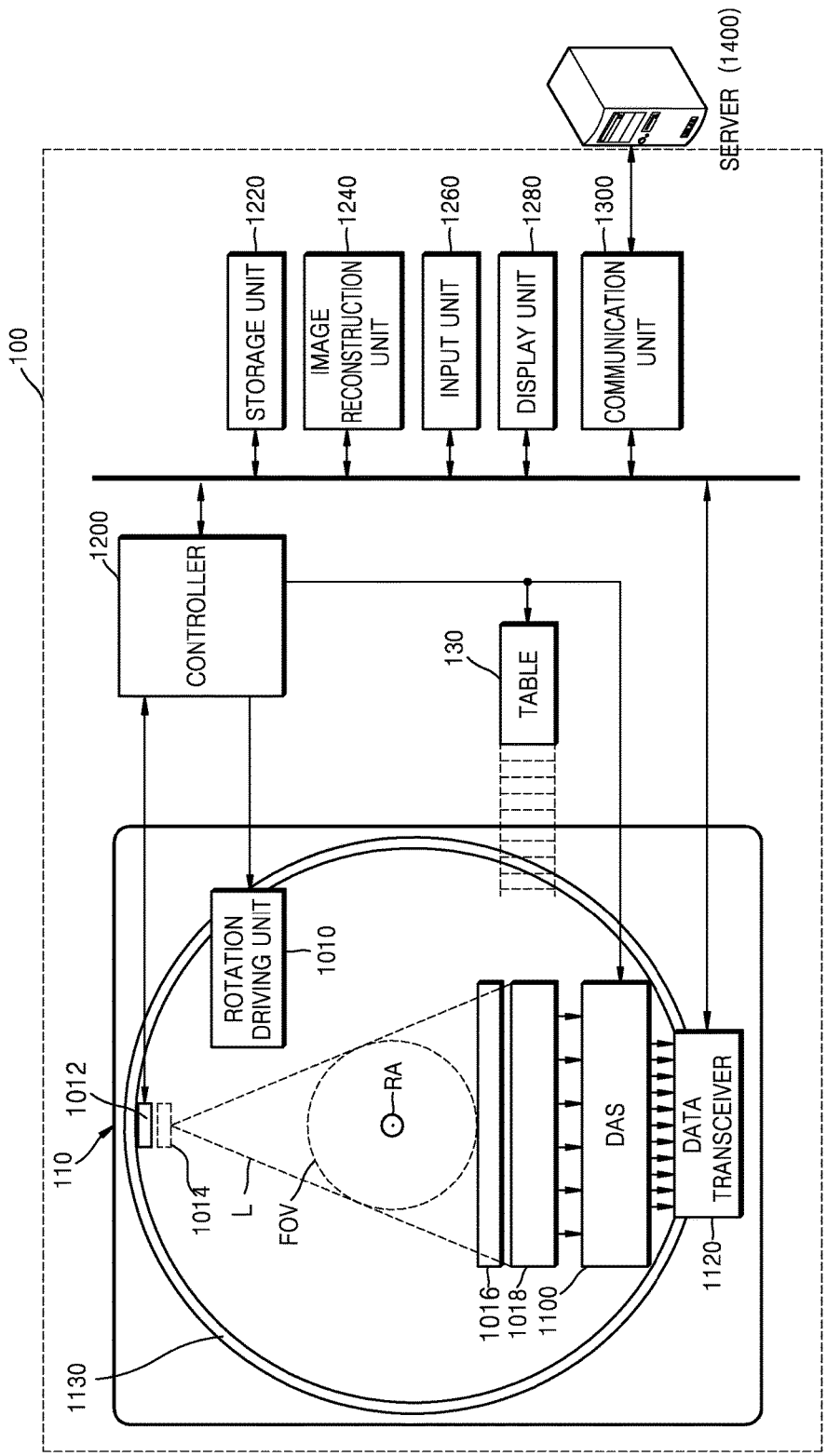
FIG. 10 is a block diagram illustrating an overall configuration of a CT system according to an exemplary embodiment.

FIG. 10 is a block diagram illustrating an overall configuration of a CT system 100 according to an exemplary embodiment.

Referring to FIGS. 1 and 10, the CT system 100 according to the exemplary embodiment may include a gantry unit 110 and a table 130 on which an subject 120 is placed. The CT system 100 may further include a controller 1200, a storage unit 1220, an image reconstruction unit 1240, an input unit 1260, a display unit 1280, and a communication unit 1300. The gantry unit 110 may include an X-ray generator 1012, a collimator 1014, an X-ray detector 1018, a rotation driving unit 1010, a DAS 1100, and a data transceiver 1120. The gantry unit 110 may include a ring type rotation frame 1130 that is rotatable with respect to a predetermined rotation axis (RA). The rotation frame 1130 may have a disc type. The rotation frame 1130 may include the X-ray generator 1012 and the X-ray detector 1018 that are facing each other to have a predetermined field of view (FOV). Also, the rotation frame 1130 may include an anti-scatter grid 1016.

In a medical image system, an X-ray that reaches the X-ray detector 1018 (or a photosensitive film) may include not only attenuated primary radiation that forms a useful image but also scattered radiation that reduces the quality of the image. In order to transmit most of the attenuated primary radiation and to reduce the transmittance of the scattered radiation, the anti-scatter grid 1016 may be located between the subject 120 and the X-ray detector 1018. The anti-scatter grid 1016 may be formed by alternately stacking strips of lead foil and an interspace material, such as, a non-hollow solid polymer material or a non-hollow solid polymer and a fiber composite material, but is not limited thereto.

The rotation frame 1130 may receive a driving signal from the rotation driving unit 1010, and may rotate the X-ray generator 1012 and the X-ray detector 1018 at a predetermined speed. The rotation frame 1130 may receive a driving signal and power from the rotation driving unit 1010, for example, by a contact method through a slip ring. Also, the rotation frame 1130 may receive a driving signal and power from the rotation driving unit 1010 through wireless communication.

The X-ray generator 1012 may generate and discharge X-rays by receiving a voltage and a current from a power distribution unit (PDU) via a slip ring through a high voltage generation unit. When the high voltage generation unit applies a predetermined voltage to the X-ray generator 1012, the X-ray generator 1012 may generate X-rays having a plurality of energy spectrums corresponding to the high voltage. The X-rays generated by the X-ray generator 1012 may be discharged as a predetermined type by the collimator 1014.

When the subject 120 placed on the table 130 is moved into the bore 112 of the gantry unit 110, X-rays L generated from the X-ray generator 1012 may be irradiated onto the subject 120 through the collimator 1014. The X-rays L transmitted through the subject 120 are detected by the X-ray detector 1018, and thus, state information of the subject 120 may be obtained. The X-ray generator 1012 may be formed to include a structure that may generate various types of X-rays, and may include a plurality of electron emitters. For example, the X-ray generator 1012 may include electron emitters that may emit electrons and an electrode unit formed of a conductive material that may emit X-rays by collision of emitted electrons. The electron emitters may be formed of a material that may emit electrons, and the material may be, for example, a metal, silicon, oxide, diamond, diamond like carbon (DLC), a carbon compound, a nitrogen compound, carbon nanotubes, etc. The X-ray generator 1012 may be formed by including a plurality of electron emitters having a ring type. When the gantry unit 110 is in operation, the location of the X-ray generator 1012 may be slightly changed, but may be fixed not to rotate. Also, the X-ray generator 1012 may be configured so that an electron gun of the X-ray generator 1012 is arranged to irradiate X-rays towards the bore 112 of the gantry unit 110, and may be any configuration that may generate X-rays.

The X-ray detector 1018 may include a single X-ray detection unit or a plurality of X-ray detection units to detect the X-rays L that are emitted from the X-ray generator 1012 and are transmitted through the subject 120 via the collimator 1014. The X-ray detection units may be formed as an array structure. The X-ray detection unit may form a single channel, but is not limited thereto. The X-ray detector 1018 may include a multi-layer structure that includes a semiconductor layer and an electrode. The X-ray detector 1018 may be formed as a ring type like the X-ray generator 1012 on a side of the X-ray generator 1012. When the gantry unit 110 is in operation, the location of the X-ray detector 1018 may be slightly changed, but may be fixed not to rotate. The X-ray detector 1018 may detect X-rays that are generated from the X-ray generator 1012 and are transmitted through the subject 120, and may generate an electrical signal in response to the strength of the detected X-rays.

The X-ray detector 1018 may be connected to the DAS 1100. An electrical signal generated from the X-ray detector 1018 may be collected at the DAS 1100. The electrical signal generated from the X-ray detector 1018 may be collected at the DAS 1100 by wire or wirelessly. Also, the electrical signal generated from the X-ray detector 1018 may be provided to, for example, an analogue/digital converter through an amplifier. According to a slice thickness of the number of slices, a portion of data collected at the X-ray detector 1018 may be provided to the image reconstruction unit 1240. The image reconstruction unit 1240 may select a portion of the data. The digital signal may be provided to the image reconstruction unit 1240 through the data transceiver 1120. The digital signal may be transmitted to the image reconstruction unit 1240 by wire or wirelessly through the data transceiver 1120.

The controller 1200 may control operations of each of the modules of the CT system 100. For example, the controller 1200 may control the operations of the table 130, the collimator 1014, the rotation driving unit 1010, the DAS 1100, the storage unit 1220, the image reconstruction unit 1240, the input unit 1260, the display unit 1280, and the communication unit 1300. The image reconstruction unit 1240 may receive data (for example, pure data before processing) obtained from the DAS 1100 through the data transceiver 1120, and may perform a process of pre-processing the data. The process of pre-processing may include, for example, a correction process with respect to non-uniform sensitivity between channels and a correction process with respect to signal loss due to a rapid reduction of intensity of signals or an X-ray absorbent such as a metal. Data output from the image reconstruction unit 1240 may be referred to as raw data or projection data. The projection data may be stored in the storage unit 1220 together with imaging conditions (for example, a tube voltage or an imaging angle, etc.) when the data is obtained. The projection data may be a collection of data values corresponding to the intensity of an X-rays transmitted through an subject. The storage unit 1220 may include at least one of a flash memory type, a hard disk type, a multimedia card micro type, a card type memory (SD or XD memory etc.), a Random Access Memory (RAM), a Static Random Access Memory (SRAM)), a Read-Only Memory (ROM), an Electrically Erasable Programmable Read-Only Memory (EEPROM), a Programmable Read-Only Memory (PROM), a magnetic memory, a magnetic disc, and an optical disc.

Also, the image reconstruction unit 1240 may reconstruct a cross-sectional image with respect to a subject by using the obtained projection data set. The cross-sectional image may be a 3-dimensional (3D) image. In detail, the image reconstruction unit 1240 may generate a 3D image with respect to the subject by using a cone-beam reconstruction method based on the obtained projection data set. External inputs with respect to an X-ray tomography conditions and an image processing conditions may be received through the input unit 1260. The conditions of X-ray tomography may be, for example, a plurality of tube voltages, energy value setting of a plurality of X-rays, selection of an imaging protocol, selection of an image reconstruction method, FOV region setting, the number of slices, a slice thickness, setting of image post-processing parameters, etc. The image processing conditions may be image resolution, setting an attenuation coefficient of an image, setting a combination ratio of an image, etc. The input unit 1260 may include devices to receive an application of a predetermined pressure from the outside. The input unit 1260 may include a microphone, a keyboard, a mouse, a joy stick, a touch pad, a touch pen, a voice recognizer, a gesture recognizer, etc. The display unit 1280 may display an image reconstructed by the image reconstruction unit 1240. The transmission and receiving of data and power between the elements described above may be performed by using at least one of wired, wireless, and optical communication. The communication unit 1300 may perform communication with external devices, external medical apparatuses, etc. through the server 1400.

In a CT system according to the exemplary embodiment, intakes and outlets are respectively formed in a first surface and a second surface of a rotor of a gantry unit, and thus, an air flow inside the rotor may be induced.

According to the exemplary embodiment, the intakes and outlets may also be formed in assembly elements mounted in the rotor, and thus, airflow inside the assembly elements may be induced.

Also, according to the exemplary embodiment, the necessity of fans in the CT system is reduced, and thus, noise may be reduced.

While exemplary embodiments have been particularly shown and described above, it will be understood by those of ordinary skill in the art that various changes in form and details may be made therein without departing from the spirit and scope of the inventive concept as defined by the following claims.

What is claimed is:
1. A computed tomography (CT) apparatus having a cooling system comprising:
   a gantry unit comprising:
     a rotor; and
     an assembly component;
   an intake provided through a first surface of the rotor; and
   an outlet provided through a second surface opposite to
     the first surface of the rotor, wherein the gantry unit is cooled by air moving through the intake and the outlet due to a rotation force or a centrifugal force generated by a rotation movement of the rotor, and wherein the first surface and the second surface are substantially parallel with each other and are separated from each other along an axial direction of the rotor.

2. The CT apparatus of claim 1, wherein the intake extends along a radial direction of the rotor at an angle between 0 and 90 degrees from a tangent line extending along a rotational direction of the rotor, the tangent line extending from an inner surface of the rotor provided between the first and the second surfaces.

3. A computed tomography (CT) apparatus having a cooling system comprising:
 a gantry unit comprising:
  a rotor; and
  an assembly component;
 an intake provided on a first surface of the rotor; and
 an outlet provided on a second surface opposite to the first surface of the rotor,
 wherein the gantry unit is cooled by air moving through the intake and the outlet due to a rotation force or a centrifugal force generated by a rotation movement of the rotor, and
 wherein the intake protrudes toward an exterior of the first surface of the rotor.

4. The CT apparatus of claim 3, wherein the intake comprises a through-hole passing through the first surface of the rotor, and comprises a protrusion unit protruding from the first surface from a portion of the first surface adjacent to the through-hole.

5. The CT apparatus of claim 4, wherein a first portion of the protrusion unit comprises a bending unit that is bent towards the through-hole and a second portion of the protrusion unit opposite to the first portion is attached to the first surface.

6. The CT apparatus of claim 1, wherein the outlet extends along a radial direction of the rotor at an angle between 90 and 180 degrees from a tangent line extending along a rotational direction of the rotor, the tangent line extending from an inner surface of the rotor provided between the first and the second surfaces.

7. The CT apparatus of claim 1, wherein the outlet protrudes towards an interior of the rotor from the second surface of the rotor.

8. The CT apparatus of claim 7, wherein the outlet comprises a through-hole passing through the second surface of the rotor, and comprises a protrusion unit protruding towards the interior of the rotor from a portion of the second surface adjacent to the through-hole.

9. The CT apparatus of claim 8, wherein a first portion of the protrusion unit comprises a bending unit that is bent towards the hole and a second portion of the protrusion unit opposite to the first portion is attached to the first surface.

10. The CT apparatus of claim 1, wherein the second surface faces the first surface.

11. The CT apparatus of claim 1, wherein the assembly component is mounted inside of the rotor.

12. The CT apparatus of claim 1, further comprising:
 a component intake provided on a first surface of the component; and
 a component outlet provided on a second surface of the component.

13. A computed tomography (CT) apparatus having a cooling system comprising:
 a gantry unit comprising:
  a rotor; and
  at least one assembly element;
 at least one intake provided in through a first surface of the at least one assembly element; and
 at least one outlet provided through a second surface opposite to the first surface of the at least one assembly element,
 wherein the gantry unit is cooled by air moving through the at least one intake and the at least one outlet due to a rotation force or a centrifugal force generated by a rotation movement of the rotor, and
 wherein the first surface and the second surface are substantially parallel with each other and are separated from each other along an axial direction of the rotor.

14. The CT apparatus of claim 13, wherein the intake extends along a radial direction of the rotor at an angle between 0 and 90 degrees from a tangent line extending along a rotational direction of the rotor, the tangent line extending from an inner surface of the rotor provided between the first and the second surfaces.

15. A computed tomography (CT) apparatus having a cooling system comprising:
 a gantry unit comprising:
  a rotor; and
  at least one assembly element;
 at least one intake provided in a first surface of the at least one assembly elements; and
 at least one outlet provided in a second surface opposite to the first surface of the at least one assembly element,
 wherein the gantry unit is cooled by air moving through the at least one intake and the at least one outlet due to a rotation force or a centrifugal force generated by a rotation movement of the rotor, and
 wherein the at least one intake protrudes towards an exterior of the first surface of the at least one assembly element.

16. The CT apparatus of claim 15, wherein the at least one intake comprises at least one hole passing through the first surface of the at least one assembly element towards an interior of the at least one assembly element, and comprises a protrusion unit protruding on the first surface from a portion of the first surface adjacent to the at least one hole.

17. The CT apparatus of claim 16, wherein an upper portion of the protrusion unit comprises a bending unit that is bent towards the at least one hole.

18. The CT apparatus of claim 13, wherein the at least one outlet extends along a radial direction of the rotor at an angle between 90 and 180 degrees from a tangent line extending along a rotational direction of the rotor, the tangent line extending from an inner surface of the rotor provided between the first and the second surfaces.

19. The CT apparatus of claim 13, wherein the at least one outlet take protrudes towards an interior of the at least one assembly element from the second surface of the at least one assembly element.

* * * * *